United States Patent [19]

Byng

[11] Patent Number: 4,920,052
[45] Date of Patent: Apr. 24, 1990

[54] PROCESS FOR PRODUCING GLUCOSE ISOMERASE

[75] Inventor: Graham S. Byng, Elkhart, Ind.

[73] Assignee: Miles Inc., Elkhart, Ind.

[21] Appl. No.: 152,481

[22] Filed: Feb. 5, 1988

[51] Int. Cl.$^5$ .......................... C12N 9/92; C12R 1/01
[52] U.S. Cl. ................... 435/234; 435/252.1; 435/276; 435/822
[58] Field of Search ............... 435/41, 234, 252.1, 435/276, 822, 94

[56] References Cited

U.S. PATENT DOCUMENTS

| | | | |
|---|---|---|---|
| 2,950,228 | 8/1960 | Marshall | 195/66 |
| 3,383,245 | 5/1968 | Scallet et al. | 127/53 |
| 3,616,221 | 10/1971 | Takasaki et al. | 195/31 |
| 3,625,828 | 12/1971 | Brownewell | 195/66 |
| 3,779,869 | 12/1973 | Zienty | 195/68 |
| 3,979,261 | 9/1976 | Outtrup | 195/65 |
| 4,061,539 | 12/1977 | Lee | 195/31 |
| 4,348,480 | 9/1982 | Brownewell | 435/234 |

OTHER PUBLICATIONS

Suekane, M. et al., *Z. Allgemeine Mikrobiologie* 21, 457 (1981).

*Primary Examiner*—Robert A. Wax
*Assistant Examiner*—Carol M. Geckle
*Attorney, Agent, or Firm*—Jerome L. Jeffers

[57] ABSTRACT

A glucose isomerase useful for the conversion of glucose to fructose can be prepared by growing under aerobic conditions a culture of a species of Microbacterium in a medium containing appropriate nutrients and then recovering the enzyme.

10 Claims, No Drawings

PROCESS FOR PRODUCING GLUCOSE ISOMERASE

BACKGROUND OF THE INVENTION

The present invention relates to a process for producing glucose isomerase by culturing strains of Microbacterium or mutations thereof.

Sweet syrups are widely used in the baking, confectionery and beverage industries, for example. These syrups generally consist of sucrose (cane sugar) or dextrose-containing products obtained from starch hydrolysis as the principal sweetening agent. When a syrup is needed that is sweeter than that obtained from sucrose, an invert sugar syrup is employed. This is produced by acid hydrolysis of sucrose to produce a mixture of about 50 percent glucose (dextrose) and about 50 percent fructose (levulose). While glucose is somewhat less sweet than sucrose, fructose is considerably sweeter than sucrose so that the overall sweetness is increased as compared to sucrose.

It is well known that dextrose can be converted under alkaline conditions to fructose. This conversion has great potential value in the production of sweet syrups. However, the alkaline conversion has not been commercially successful because the alkaline reaction produces an undersirably high ash level in the product syrup which is uneconomical to remove. The syrup is not acceptable unless this ash is removed. Alkaline isomerization and its attendent problems are discussed in U.S. Pat. No. 3,383,245.

The prior art then turned to an enzyme conversion of glucose to fructose. It was found that species of *Pseudomonas hydrophila, Streptomyces flavovirens, Streptomyces achromogenus, Streptomyces echinatur, Streptomyces albus, Streptomyces olivaceus, Bacillus coagulans, Microbacterium arborescens* (formerly classified as *Flavobacterium arborescens* and *Bacillus licheniformis*, for example, could be grown in appropriate nutrient media to form enzymes having glucose isomerase properties. This is described, for example, in U.S. Pat. Nos. 2,950,228, 3,616,221, 3,625,828, 3,979,261, 4,061,539 and 4,348,480. The screening of many strains of bacteria for the production of glucose isomerase was reported by suekane, M. et al., *Z. Alegemeine Microbiologie* 21, 457 (1981). Suekane et al. reported that *M. lacticum* and *Brevibacterium imperiale* (reclassified as *M. imperiale*) did not grow on xylose and did not produce glucose isomerase. *M. laevaniformens* was formerly classified as *Corynebacterium laevaniformans*. Suekane et al. tested several species of Corynebacterium and reported that none of these species produced glucose isomerase. Consequently, none of the known prior art suggests the use of strains of the species *Microbacterium imperiale, M. lacticum, M. ammoniaphilum* or *M. laevaniformans* to produce a glucose iosmerase.

SUMMARY OF THE INVENTION

The present invention is directed to a process for producing glucose isomerase which comprises growing a culture of Microbacterium or mutations thereof under aerobic conditions in a medium containing appropriate nutrients, and then recovering the enzymes. Suitable strains of Microbacterium include strains of the species *M. imperiale, M. lacticum, M. ammoniaphilum,* and *M. laevaniformans*, or mutations thereof.

DETAILED DESCRIPTION OF THE INVENTION

The present invention utilizes strains of Microbacterium or mutations thereof for the production of glucose isomerase. It has been discovered that certain strains are capable of producing glucose isomerase in significant quantities. These strains display a substantial level of constitutive enzyme activity in the absence of the normal inducer, xylose. For example, these Microbacterium species produce glucose isomerase when grown on nutrient medium containing lactose, whereas *M. arborescens* does not produce glucose isomerase under these conditions. Suitable Microbacterium species for the production of glucose isomerase include: *M. imperiale, M. lacticum, M. ammomiaphilum, M. laevaniformans*, and mutations thereof. Strains of these Microbacterium species are currently available form the American Type Culture Collection, Rockville, Md., under the identification numbers ATCC 8365, ATCC 8180, ATCC 15354 and ATCC 15953, respectively.

Mutations of the Microbacterium species capable of producing glucose isomerase can be prepared as known in the art. For example, the mutations may arise by spontaneous mutations. Mutations can also be produced by several techniques, including chemical mutagenesis induced by ethyl methane sulfonate, nucleotide-base analogues, sodium bisulfite and the like, physical mutagenesis induced by heat, gamma irradiation, ultraviolet irradiation and the like, oligonucleotide-directed mutagenesis, DNA deletions, DNA insertions and the like. Finally, mutations can be produced by wellknown genetic engineering techniques to (a) increase the production of glucose isomerase, (b) improve the growth properties of the microorganisms and the like. Mutants of the disclosed Microbacterium species can be selected and/or screened for resistance to 2-deoxyglucose, as described in U.S. Pat. No. 4,355,103.

The Microbacterium species are maintained on agar slants, preferably Nutrient agar (Difco Laboratories, Detroit, Mich.), and can be cultivated on a variety of media containing appropriate nutrients. Preferably, the medium contains sources of carbon, nitrogen and inorganic salts. Illustrative nitrogen sources are brewer's yeast extract, hydrolyzed animal protein and the like. Illustrative inorganic salts include ammonium sulfate, dipotassium phosphate, magnesium sulfate, manganese sulfate and the like. A preferred medium contains hydrolyzed animal protein, corn steep liquor, a brewer's yeast extract, buffer (inorganic) salts, and a carbohydrate. Suitable carbohydrates include xylose, lactose, hydrolysates of polymers and the like.

The organism is grown under aerobic fermentation conditions at a temperature of from about 30° C. to about 35° C. The preferred growth temperature is 33° C. The pH of the growth medium shoukd be maintained in the range from about 6.5 to about 7.5. The preferred pH is 7.0. An initial pH of about 7.0 for the growth medium is preferred. Maxium glucose isomerase activity is generally attained in about 48 to about 72 hours.

The glucose isomerase of the present invention is formed inside the bacterial cells which grow during its production. The cells can be separated from the fermentation beer by well-known means, such as filteration or centrifurgation, and used directly as a source of glucose isomerase. Such cells can be agglomerated and the enzyme activity immobolized therein by well-known techniques, such as the glutaraldehyde treatment disclosed in U.S. Pat. No. 3,779,869. Alternatively, the cells could be ruptured either mechanically, by autolysis or by other enzymatic means, and the soluble enzyme separated from the cell debris. The soluble enzyme can be used directly or it can be immobilized on a suitable carrier by well-known techniques.

The invention will be described in further detail in the following example.

EXAMPLE

Portions of cultures of Microbacterium species were each transferred from the nutrient agar plates to 250 ml baffled flasks containing 50 ml of an aqueous medium comprising 1% hydrolyzed animal protein (Bacto-Tryptone, obtained from Difco Laboratories), 1% dried corn steep liquor (Roquettes freres), 1% yeast extract (Difco), 1% potassium monohydrogen phosphate, 0.5% potassium dihydrogen phosphate and 2% xylose or lactose. The initial pH of the medium was about 7.0. The flasks were then incubated at 33° C. for 72 hours on a rotary shaker rotating at 250 rpm. After incubation the cultures were assayed for glucose isomerase activity by the method described in U.S. Pat. No. 4,348,480. The results are shown in the following table. Glucose isomerase activity is expressed in units (GIU) which equal the micromoles of fructose formed per minute under conditions of the assay.

| Species | GIU/L | |
|---|---|---|
| | lactose | xylose |
| Microbacterium lacticum | 51 | 303 |
| Microbacterium imperiale | 907 | 12,687 |
| Microbacterium ammoniaphilum | 705 | 303 |
| Microbacterium laevaniformans | 253 | 303 |
| Flavobacterium arborescens* | 0** | 3,303** |

*reclassified as *M. arborescens*
**data derived from U.S. Pat. 4,061,539, converted to GIU/L

What is claimed is:

1. A process for the production of a glucose isomerase which comprises growing a culture of a Microbacterium species selected from the group consisting of *M. lacticum, M. imperiale, M. ammoniaphilum, M. laevaniformans* and glucose isomerase-producing mutants thereof in a medium containing appropriate nutrients for a sufficient time to produce a recoverable quantity of the enzyme and recovering the enzyme from the culture.

2. The process of claim 1 wherein the growing is performed aerobically.

3. The process of claim 1 wherein said species is *M. lacticum*.

4. The process of claim 1 wherein said species is *M. imperiale*.

5. The process of claim 1 wherein said species is *M. ammoniaphilum*.

6. The process of claim 1 wherein said species is *M. laevaniformans*.

7. The process of claim 1 wherein said culture is a glucose isomerase-producing mutant of *M. lacticum*.

8. The process of claim 1 wherein said culture is a glucose isomerase-producing mutant of *M. imperale*.

9. The process of claim 1 wherein said culture is a glucose isomerase-producing mutant of *M. ammoniaphilum*.

10. The process of claim 1 wherein said culture is a glucose isomerase-producing mutant of *M. laevaniformans*.

* * * * *